United States Patent
Gessert et al.

(10) Patent No.: US 9,513,327 B2
(45) Date of Patent: Dec. 6, 2016

(54) TESTING OF ULTRASONIC IMAGING SYSTEMS

(71) Applicant: Acertara Acoustic Laboratories LLC, Longmont, CO (US)

(72) Inventors: James Gessert, Loveland, CO (US); G. Wayne Moore, Lyons, CO (US)

(73) Assignee: Acertara Acoustic Laboratories LLC, Longmont, CO (US)

( * ) Notice: Subject to any disclaimer, the term of this patent is extended or adjusted under 35 U.S.C. 154(b) by 291 days.

(21) Appl. No.: 14/336,117

(22) Filed: Jul. 21, 2014

(65) Prior Publication Data

US 2016/0018460 A1    Jan. 21, 2016

(51) Int. Cl.
| | |
|---|---|
| G01N 29/24 | (2006.01) |
| G01R 31/26 | (2014.01) |
| G01N 29/26 | (2006.01) |
| G01N 29/28 | (2006.01) |

(52) U.S. Cl.
CPC ....... *G01R 31/2601* (2013.01); *G01N 29/2437* (2013.01); *G01N 29/262* (2013.01); *G01N 29/28* (2013.01)

(58) Field of Classification Search
CPC .. G01N 29/24; G01N 29/2437; G01H 3/005; G01R 31/2601
USPC .......................................... 73/1.82; 702/116
See application file for complete search history.

(56) References Cited

U.S. PATENT DOCUMENTS

| | | | |
|---|---|---|---|
| 4,651,567 A | 3/1987 | Sandhu | |
| 4,722,346 A | 2/1988 | Chen | |
| 4,936,138 A | 6/1990 | Cushman et al. | |
| 6,035,696 A | 3/2000 | Kiefer et al. | |
| 6,122,968 A | 9/2000 | Vandervalk | |
| 6,323,661 B1 * | 11/2001 | Wildes ................ | G01N 27/041 324/715 |
| 6,552,841 B1 | 4/2003 | Lasser et al. | |
| RE40,456 E | 8/2008 | Bates | |
| 7,726,172 B2 | 6/2010 | Moore et al. | |
| 2005/0096554 A1 | 5/2005 | Dudik et al. | |
| 2007/0038096 A1 | 2/2007 | Seip et al. | |
| 2007/0234807 A1 * | 10/2007 | Moore .................... | G01H 3/12 73/570 |
| 2012/0165665 A1 | 6/2012 | Sandstrom et al. | |
| 2012/0184849 A1 | 7/2012 | Sandstrom et al. | |
| 2012/0210795 A1 * | 8/2012 | Ohm ................. | G01N 29/2437 73/606 |
| 2012/0323122 A1 | 12/2012 | Okubo | |
| 2014/0020469 A1 | 1/2014 | Gessert et al. | |
| 2014/0071789 A1 | 3/2014 | Brodsky et al. | |

\* cited by examiner

*Primary Examiner* — Peter Macchiarolo
*Assistant Examiner* — Anthony W Megna Fuentes
(74) *Attorney, Agent, or Firm* — Marsh Fischmann & Breyfogle LLP; Jonathon A. Szumny (57) ABSTRACT

Devices and methods for testing the operation of acoustic devices such as ultrasonic probes. The disclosed devices and methods identify failures of individual piezoelectric elements of various types of ultrasonic probes free of family-specific adapters to interface with such probes and free of acoustic coupling fluids or the like to establish acoustic coupling with the probes. In one arrangement, a testing appliance is disclosed that includes a testing unit and first and second probes electrically connected thereto. After an operator has established electrical connections between the first probe and a first contact of a connector assembly of the acoustic probe and between the second probe and a ground return path of the connector assembly, the testing device may pass a current through an electric circuit between the first and second probes and determine one or more corresponding electrical quantities of the circuit for establishing statuses of the probe.

25 Claims, 11 Drawing Sheets

MAIN.PY

MANUFACTURER: PHILIPS

SYSTEM: iU-22

ARRAY TYPE: SECTOR

ARRAY MODEL: C10-3v

TESTING OF ULTRASONIC IMAGING SYSTEMS

BACKGROUND

1. Field of the Invention

This application relates generally to acoustic systems and probes and, more specifically, to methods and systems for testing acoustic systems including ultrasonic probes and transducers.

2. Relevant Background

Acoustic (e.g., ultrasonic) imaging is an important technique that may be used at different acoustic frequencies for varied applications that range from medical imaging to nondestructive testing of structures. The techniques generally rely on the fact that different structures have different acoustic impedances, allowing characterization of structures and their interfaces from information embodied by the different scattering patterns that result. While most applications use radiation reflected from structures, some techniques make use of information in transmitted patterns also.

Transmission of acoustic radiation (e.g., acoustic waves) towards a target and receipt of the scattered radiation may be managed by modern acoustic-imaging systems, each of which may take a variety of forms. For example, many modern systems are based on multiple-element array transducers that may have linear, curved-linear, phased-array or similar characteristics and which may be embodied in an acoustic probe. Summing the contributions of the multiple elements that form a transducer array allows images to be formed. However, the failure of a small number of elements in a given array, or even of a few defective receive channels in the acoustic system itself, may not be readily perceptible to users because of the averaging effect of summing many elements to form an acoustic beam. Furthermore, the failure of even a small number of elements or receive channels can significantly degrade the performance of acoustic imaging systems, notably in certain modes of operation like those known as "Doppler" or "near-field" imaging modes.

SUMMARY

While appliances (e.g., testing devices or systems) have previously been developed to test the operation of array elements of acoustic systems and probes (e.g., to determine whether some of the array elements have failed), the appliances have been relatively complex and/or suffer from a number of other inefficiencies that can limit their usefulness. For instance, some existing testing appliances require different adapters to allow the appliances to interface with different acoustic probes necessarily increasing the complexity and cost of the testing appliances. As another example, some existing testing appliances require use of water or the like for acoustic coupling between the acoustic probe and the testing appliance and/or can only isolate failures to a general region of a resulting image (and thus to a general region of elements). Still further, many existing testing appliances require connection to an external computer (e.g., desktop, tablet, etc.) for processing signals received from the testing appliance and determining whether or not the probe is functioning properly.

The inventors have thus determined that devices, methods, and the like (e.g., utilities) are needed to test acoustic probes in manners that do not require sets of family specific adapters to interface with a respectively plurality of different probes, do not require any types of acoustic coupling fluids or the like to establish acoustic coupling with the probe, and that can isolate faults down to the element level rather than just to a general region of elements. Furthermore, the inventors have determined that such utilities may include use of a hand-held, easy to operate device that provides real-time information regarding the status of individual elements of the probe free of having to interface the device with any external computing devices.

In one aspect, an appliance for testing the operation of an acoustic device that generates acoustic waves includes a housing, circuitry disposed within the housing that is configured to determine one or more electrical quantities (e.g., AC voltage, AC current) of an electrical circuit passing through a piezoelectric element of an acoustic device, a first probe electrically connected to the circuitry and that is electrically connectable to a contact of a contact array of the acoustic device that is electrically connected to the piezoelectric element via the electrical circuit, a second probe electrically connected to the circuitry and that is electrically connectable to a ground return path of the acoustic device via the electrical circuit, and a display attached to the housing and in electrical communication with the circuitry, where the display presents graphical images of the contact array and one or more values (e.g., capacitance, resistance, etc.) derived from the determined electrical quantities. For instance, the circuitry may use the determined electrical quantities to determine a complex impedance between the first and second probes and the determined complex impedance to determine at least one of either the capacitance or the resistance between the first and second probes.

In one arrangement, the display may present graphical images of a first contact array of a first acoustic device and a second contact array of a second acoustic device different than the first acoustic device. In another arrangement, the display may present a graphical indication of a status of one or more piezoelectric elements of the acoustic device based on the determined electrical quantities. For instance, the status may be one of functioning at or above a threshold level of acceptability or not functioning above the threshold level of acceptability.

In another aspect, a method for testing the operation of an acoustic device that generates acoustic waves includes first receiving, from a display of an electronic measurement instrument (e.g., an acoustic probe testing appliance), a graphical indication of a contact array of an acoustic device to be tested, where the graphical indication of the contact array includes a graphical indication of a first contact of the contact array, and where the graphical indication of the first contact is different than the graphical indication of other contacts of the contact array. For instance, the electronic measurement instrument may include a memory storing a list of various different acoustic probes (e.g., different as to model, manufacturer, etc.) in addition to the specific different contact array configurations of the different probes (e.g., where each contact is directly electrically connected to a different respective element of the probe). In this regard, a user may be able to input a specific model or type of acoustic probe to be tested into the electronic measurement instrument and then receive, on a display of the instrument, a graphical indication of the appropriate contact array configuration.

The method may then include establishing a first electrical connection between a first probe of the electronic measurement instrument and the first contact of the acoustic device (e.g., using the different graphical representation of the first contact), establishing a second electrical connection between a second probe of the electronic measurement instrument and a ground return path of the acoustic device, and second receiving, from the display, in response to the established first and second electrical connections, a graphical indication of a status of the acoustic device. For instance, the second receiving step may include receiving a graphical indication of a status of a first piezoelectric element (e.g., functioning properly, failed, etc.) of a piezoelectric element array of the acoustic device that is in direct electrical communication with the first contact. The user may then be able to perform the method with respect to additional contacts of the contact array to determine different statuses thereof.

In a further aspect, a method for the testing operation of an acoustic device that generates acoustic waves includes first presenting, on a display of an electronic measurement instrument, a graphical representation of a contact array of a multi-contact connector of an acoustic device; modifying an appearance of a first contact of the contact array relative to other contacts of the contact array on the display; determining, by the electronic measurement instrument, a value of at least one electrical quantity of an electrical circuit that passes through a first piezoelectric element of the acoustic device that is in direct electrical communication with the first contact; ascertaining, by the electronic measurement instrument based on the value of the at least one determined electrical quantity, a status of the acoustic device; and second presenting, on the display, the status of the acoustic device.

In one arrangement, the second presenting step includes third presenting a graphical representation of at least the first piezoelectric element and modifying an appearance of the graphical representation of at least the first piezoelectric element to indicate the status of the first piezoelectric element. For instance, the third presenting step may include presenting a graphical representation of a plurality of piezoelectric elements of the acoustic device, where the first piezoelectric element is one of the plurality of piezoelectric elements.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended to refer collectively to all reference labels that have the same primary label but different sublabels.

FIG. 6b is a close-up perspective view of a testing unit of the testing appliance of FIG. 6a.

DETAILED DESCRIPTION

Disclosed herein are testing utilities for testing and determining the operational statuses of a plurality of different acoustic devices (e.g., ultrasonic probes) free of any need to employ acoustic device-specific adapters, acoustic coupling fluids between an acoustic transducer of the acoustic device and the disclosed testing utilities, and the like. The disclosed utilities also provide electrical quantity (e.g., complex impedance, capacitance, resistance, etc.) and operational status information down to the piezoelectric element level of an acoustic device to allow operators to pinpoint problems with an acoustic device. While much of the description below makes use of specific examples in discussing various aspects of the invention, such examples are intended merely for illustrative purposes and the invention is not necessarily to be limited by any operational characteristics disclosed herein.

Figure 1:
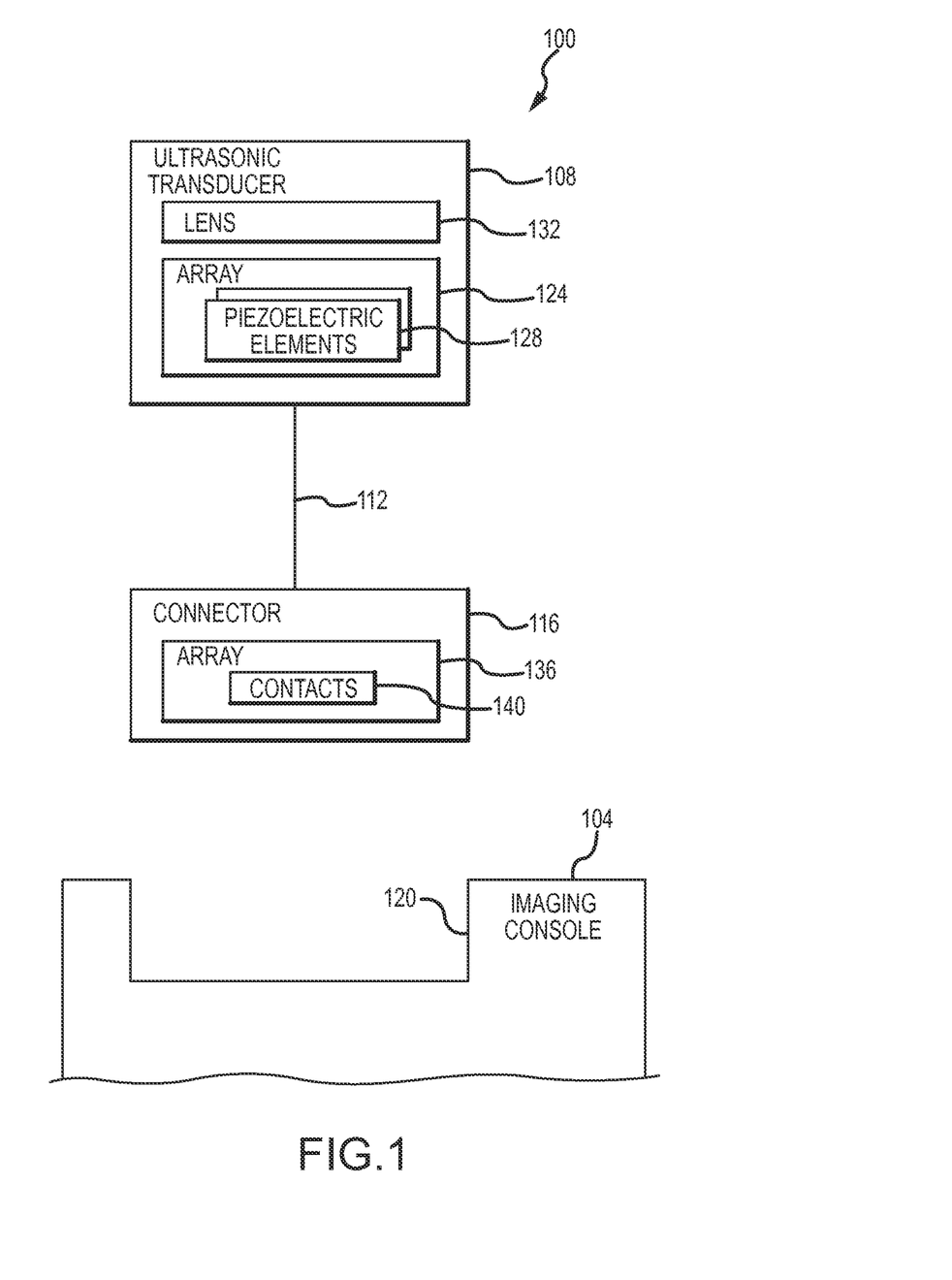
FIG. 1 is a block diagram of an ultrasonic imaging system according to one embodiment.

With initial reference to FIG. 1, a block diagram of an ultrasonic imaging system 100 that may be tested by the testing utilities disclosed herein is presented. Broadly, the system 100 includes an imaging console 104 and an ultrasonic transducer 108 (e.g., transducer head) that is electrically interconnectable to the imaging console 104 by any appropriate cable assembly 112 and a connector assembly 116, where the connector assembly 116 is configured to interface with a corresponding port 120 on the imaging console 104. The imaging console 104 transmits a drive signal to the ultrasonic transducer 108 to cause piezoelectric elements of the ultrasonic transducer 108 to transmit acoustic waves (e.g., ultrasound, ultrasonic waves) to a subject. The ultrasonic transducer 108 is then configured to receive reflection waves reflected by the interior of the subject and pass the same to the imaging console for generation of one or more corresponding images. The ultrasonic transducer 108, cable assembly 112 and connector 116 may be referred to as an "acoustic probe" or "ultrasonic probe."

The ultrasonic transducer 108 includes any appropriate array 124 of piezoelectric elements 128 (e.g., linear, curved linear, etc.) that transmit ultrasonic waves towards a subject area, where summing the contributions of the multiple piezoelectric elements 128 allows images to be formed. The ultrasonic transducer 108 also includes any appropriate lens 132 (e.g., layer of rubber) that covers the array 124 to provide electrical safety, acoustic focusing, impedance matching, facilitate disinfection, and/or the like. While not shown, the ultrasonic transducer 108 may also include one or more other components such as backing layers, electrical contacts, and the like.

Figure 2:
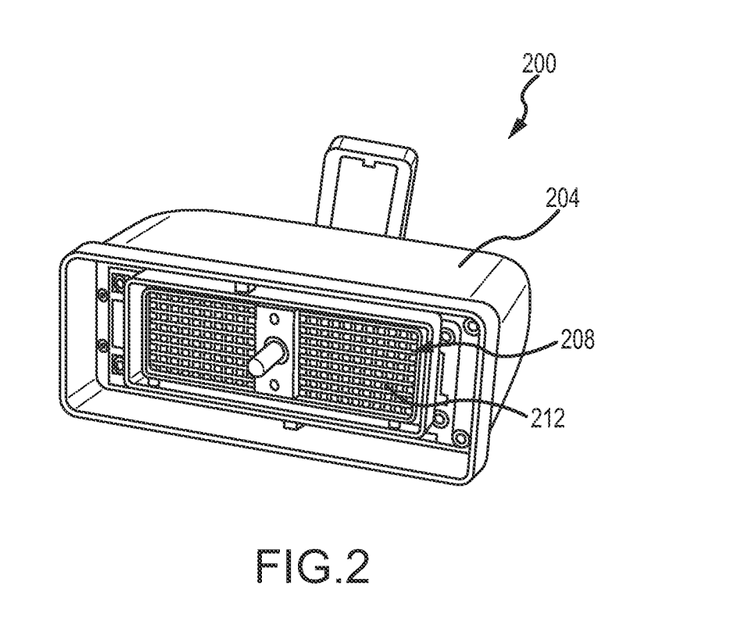
FIG. 2 is a perspective view of a multi-contact connector for electrically interconnecting an ultrasound transducer to an imaging console.

The connector assembly 116 may include any appropriate housing (e.g., shield, casing, etc.) as well as an array 136 of electrical contacts 140 (e.g., pins, flat surfaces, etc.) that are configured to electrically connect the multiple piezoelectric elements 128 to the imaging console 104. More specifically, each respective contact 140 in the array 136 is directly electrically connected to a different respective piezoelectric element 128 of the ultrasonic transducer 108 via the cable assembly 112. For instance, FIG. 2 illustrates one example of a connector assembly 200 including a housing 204 and an array 208 (e.g., array 136) of electrical contacts 212 (e.g., electrical contacts 140).

Returning to FIG. 1, the imaging console 104 may be in the form of a housing including any appropriate arrangement of circuitry, components, and the like to receive inputs, generate corresponding drive signals to be transmitted to the piezoelectric elements 128 of the ultrasonic transducer 108 over cable assembly 112 and via the respective contacts 140 of the connector assembly 116 electrically interfaced with the imaging console 104. For instance, the imaging console 104 may include a control section including any appropriate arrangement of processing units (e.g., processors, CPUs, etc.), memory (e.g., volatile memory such as random access memory or the like), storage (e.g., non-volatile such as hard disk, flash, etc.), etc. for purposes of central controlling of the operation of each section the ultrasonic imaging system 100 in conjunction with one or more developed programs or code portions. The imaging console 104 may also include any appropriate operational input section (e.g., including switches, buttons, keyboard, etc.) in communication with the control section, a transmission section (e.g., circuitry) configured to transmit drive signals to the ultrasonic transducer 108 based on signals received from the control section, a receiving section (e.g., circuitry) configured to receive reflection ultrasound reception signals under control of the control section, and one or more displays configured to display ultrasonic images of the subject under control of the control section. Various additional details of the imaging console 104 have been omitted from this discussion in the interest of brevity.

As discussed previously, existing testing devices for and manners of testing the functionality or operational status of acoustic devices suffer from one or more inefficiencies such as the requirement for different adapters for interfacing with different acoustic devices, the need to utilize one or more coupling fluids between the acoustic device and the testing devices, the inability to isolate failures down to the piezoelectric element level, the need to connect to external componentry to processes results, and the like. In this regard, and turning now to FIG. 3, a block diagram of a testing appliance 300 is illustrated that is configured to test acoustic probes (e.g., ultrasonic systems, etc.) in a manner that is free of any family-specific adapters to interface with respective probes/transducers, that is free of any acoustic coupling fluids or the like to establish acoustic coupling with the probes, and that can isolate faults down to the piezoelectric element level, among other advantages. To facilitate discussion of the testing appliance 300, reference will also be made to FIGS. 4-5 which present respective methods 400, 500 of testing the operation of an acoustic device (ultrasonic probe of FIG. 1) that generates acoustic (e.g., ultrasonic) waves. It is to be understood, however, that other methods of testing acoustic devices (e.g., including additional, fewer, or different steps) consistent with the teachings herein are encompassed by the present disclosure.

Figure 3:
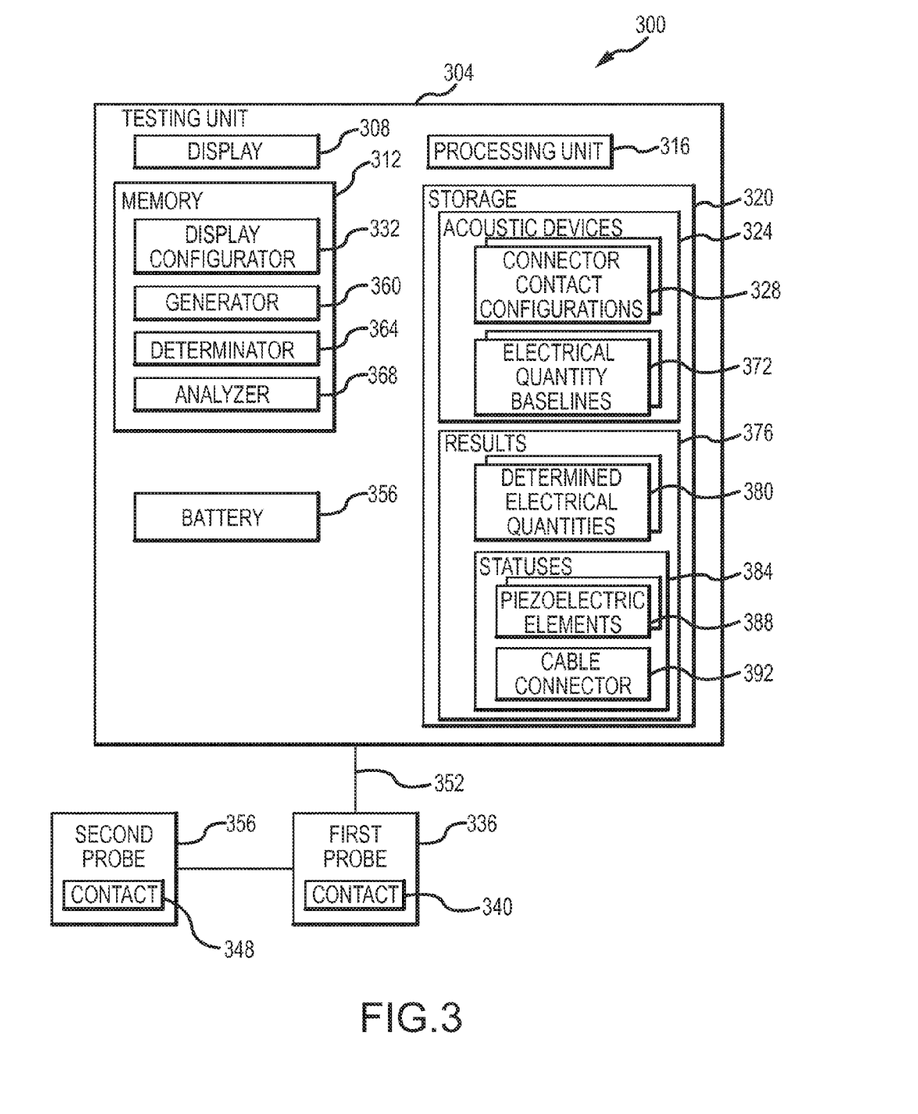
FIG. 3 is a block diagram of a testing appliance for testing the operation of an acoustic device that generates acoustic waves, such as the imaging system of FIG. 1.
Figure 4:
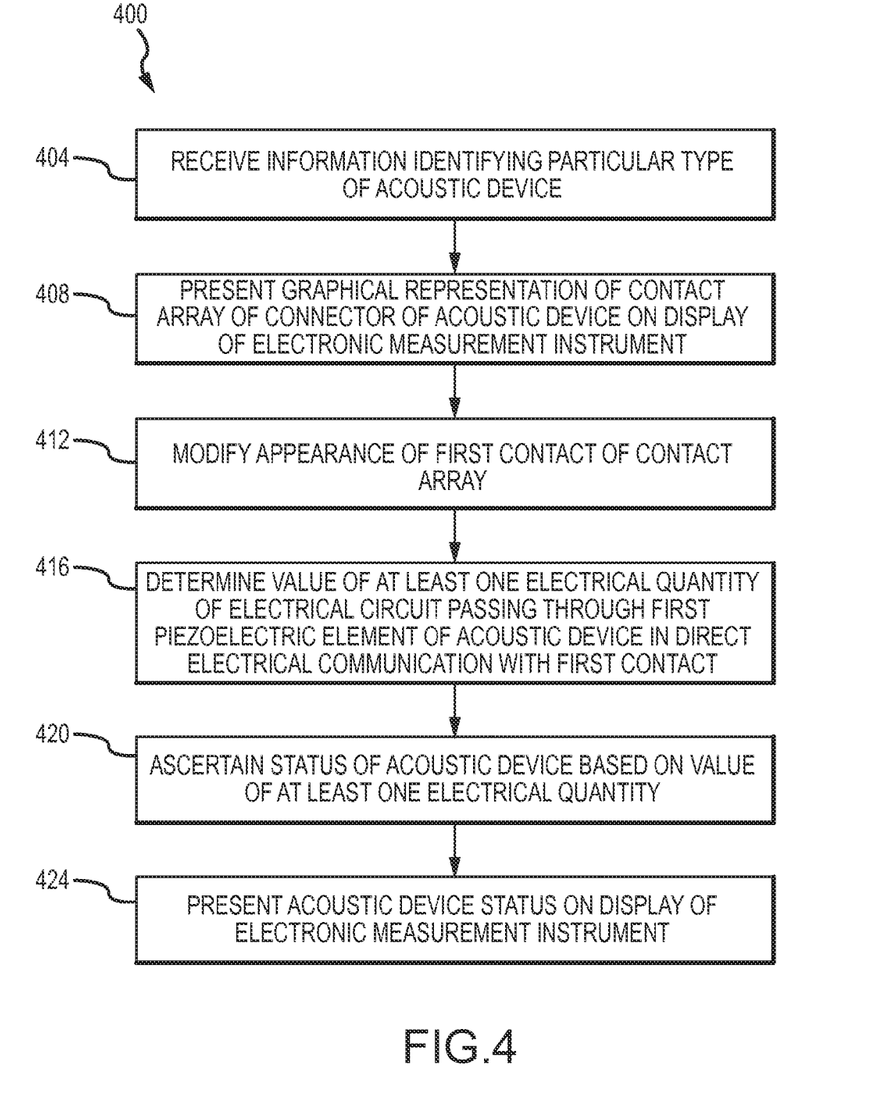
FIG. 4 is a flow diagram of a method of testing the operation of an acoustic device that generates acoustic waves according to an embodiment.
Figure 6A:
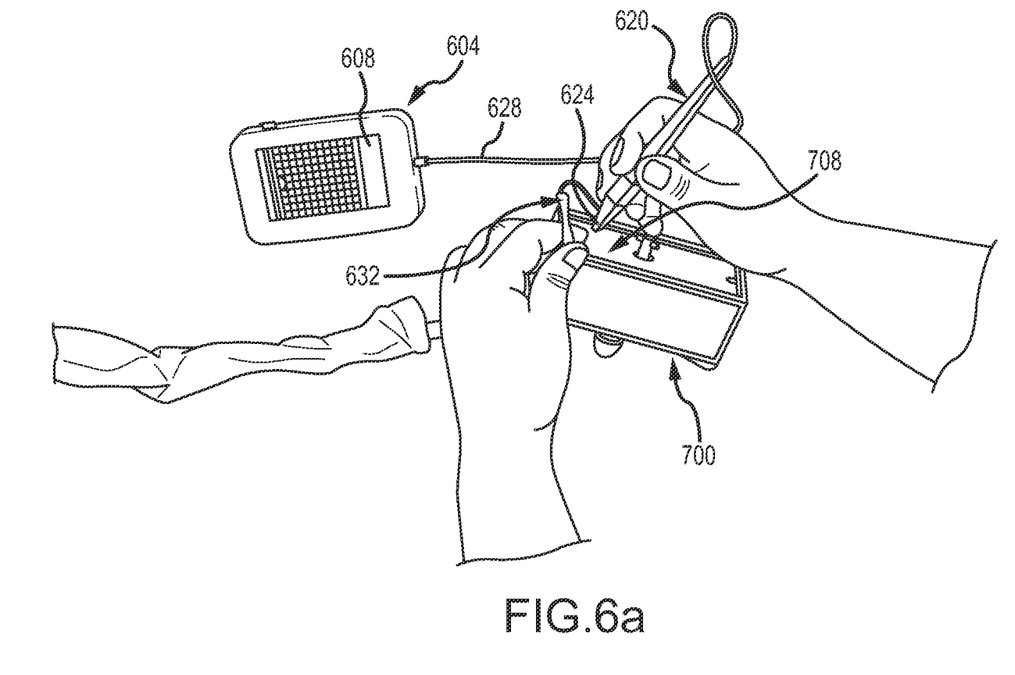
FIG. 6a is a perspective view of a testing appliance according to one embodiment, where a first probe of the testing appliance is in electrical contact with a contact array of a connector of an imaging system.
Figure 7:
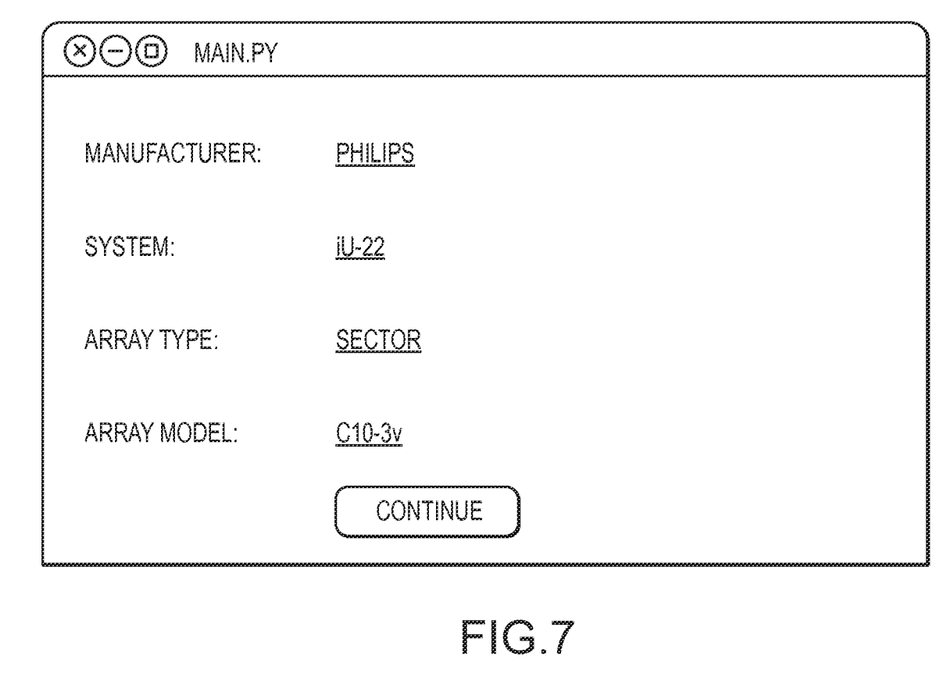
FIG. 7 is a screenshot of a display of a testing unit of the testing appliance of FIG. 6.

At 404, the method 400 of FIG. 4 may include receiving, into an electronic measurement instrument, information that identifies a particular type of acoustic device to be tested. For instance, a user may input 504 such information into a testing unit 304 of the testing appliance 300 in any appropriate manner. In one arrangement, the testing unit 304 may be in the form of a hand-held, battery-operated device including a display 308 for receiving such identifying information and presenting testing results thereon (e.g., such as testing unit 604 of FIG. 6a including display 608). With reference to the screenshot of display 608 illustrated in FIG. 7, various types of acoustic device identifying information may be inputted 504 and received 404 such as one or more of a manufacturer name, system name, probe type (e.g., cardiac and probe model), etc. The user may input 504 the identifying information by physically manipulating the display (e.g., in the case of a touch screen), a keyboard electrically connected to the testing unit 304, and/or the like.

Returning to FIG. 4, the method 400 may then include presenting 408, on the display of the electronic measurement instrument, a graphical representation of the contact array of a connector assembly of the acoustic device based on the received 404 identifying information, and modifying 412 an appearance of at least a first contact of the contact array. As shown in the block diagram of FIG. 3, the testing unit 304 may include a plurality of hardware components such as memory 312 (e.g., one or more RAM or other volatile memory modules), a processing engine or unit 316 (e.g., one or more CPUs) for executing computer readable instructions from the memory 312, storage 320 (e.g., non-volatile memory such as flash memory or the like), and/or a number of other components (e.g., input devices, output devices, interfaces, etc.), all of which may be appropriately interconnected by circuitry such as a system bus or the like (not shown). In one arrangement, a list or database of connector contact array configurations 328 may be indexed by acoustic device 324 (e.g., type, manufacturer, etc.), maintained in storage 320, and accessed by a display configurator 332 (e.g., logic, computer-readable instructions) of memory 312 as part of the presenting step 408.

For instance, the display configurator 332 may, upon receipt 404 of the acoustic device identifying information, use the received identifying information to access the specific contact array configuration 328 and present 408 the particular contact array configuration 328 on the display 308 of the testing unit 304. See graphical representation of contact array 612 on display 608 of testing unit 604 of FIG. 6b and note how the graphical appearance of a first contact 616 of the contact array 612 is different than other contacts of the contact array 612 in color (e.g., although the graphical representation of the first contact 616 may be different in one or more other regards such as contrast, shading, pattern, shape, etc.). As will be discussed in more detail below, a user may establish electrical contact with the first contact of the connector (e.g., connector assembly 700, connector assembly 116) for purposes of testing the operation of the piezoelectric element (e.g., piezoelectric element 128 of FIG. 1) that is directly electrically connected to the first contact.

In one arrangement, the display configurator 332 may be configured to sequentially modify the appearance of each of the contacts in the contact array in the display 308 (e.g., in display 608 of FIG. 6b) for purposes of testing the operation of each of the piezoelectric elements (e.g., piezoelectric elements 128) that are directly electrically connected to respective contacts of the contact array. In another arrangement, a user may be able to input into the testing unit 304 (e.g., as part of the entry of acoustic device identifying information), an indication of less than all of the piezoelectric elements to be tested. For instance, a user may input into the testing unit 304 a particular region, area or sector of piezoelectric elements 128 of the ultrasonic transducer 108 to be tested. In one arrangement, a user may utilize one or more of the testing appliances or methods of U.S. Patent App. Pub. No. 2014/0020469 to isolate one or more particular areas or regions of piezoelectric elements (and thus corresponding contacts of the contact array) to be tested, the entirety of which has been incorporated herein by reference as if set forth in full.

Figure 5:
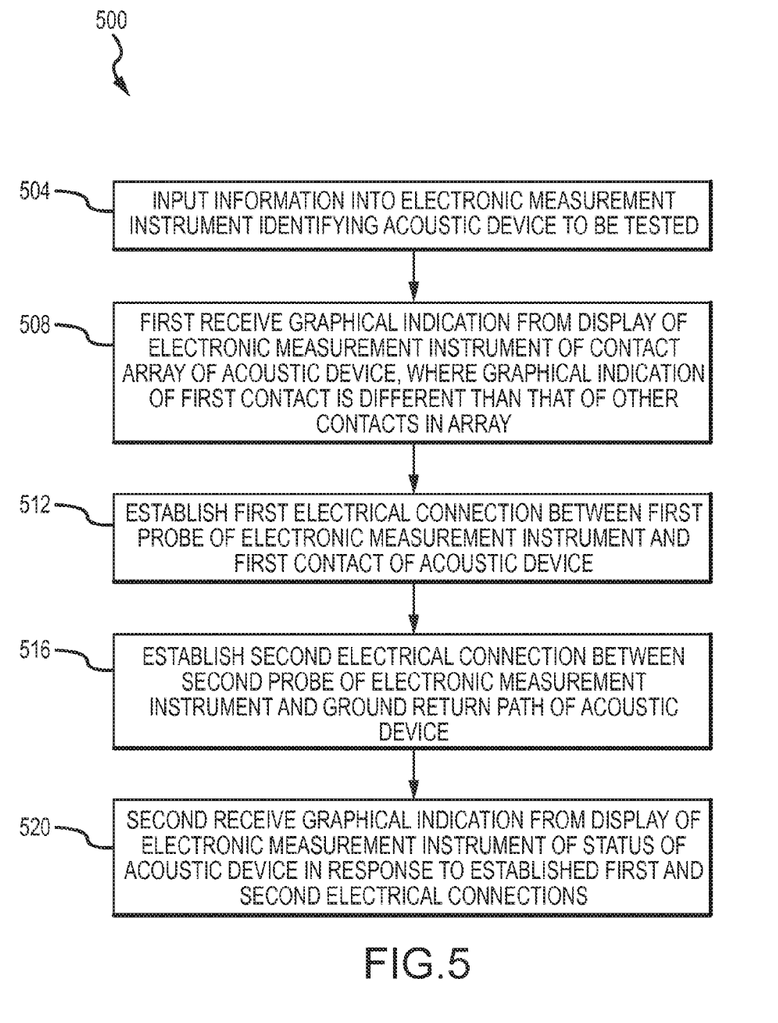
FIG. 5 is a flow diagram of a method of testing the operation of an acoustic device that generates acoustic waves according to an embodiment.

Again returning to FIG. 4, the method 400 includes determining 416 a value of at least one electrical quantity of an electrical circuit passing through a first piezoelectric element of the acoustic device, where the first piezoelectric element is in direct electrical communication with the first contact. With reference to FIGS. 3 and 5, the user may establish 512 a first electrical connection between an electrical contact 340 of a first probe 336 of the electronic measurement instrument (e.g., testing appliance 300) and the first contact 140 of the connector assembly 116 of the acoustic probe to be tested (see FIG. 1). In one arrangement, the first probe 336 may be in the form of a hand-held instrument (e.g., stylus or the like) that is electrically connected to the circuitry of the testing unit 304 (i.e., to the memory 312, processing unit 316, etc.) via any appropriate cable assembly 352. For instance, see electrical contact 624 of first probe/stylus 620 of FIG. 6a in electrical contact with a first contact (not labeled) of contact array 708 of connector 700 (e.g., first contact corresponding to the graphical representation of the first contact 616 in the display 608 of FIG. 6b), where the first probe 620 is electrically connected to the circuitry of the testing unit 604 via cable assembly 628.

A user may also establish 516 a second electrical connection between an electrical contact 348 of a second probe 344 of the testing appliance 300 and a ground return path of the acoustic device. In one arrangement, the second probe 344 may be in the form of a hand-held instrument (e.g., alligator clip, ground lead, etc.) that is electrically connected (via a cable assembly, not labeled) to the first probe 336 and thus electrically connected to the testing unit 304 via the cable assembly 352. With reference again to FIG. 6a, for instance, an electrical contact (not shown) of a second probe 632 may be electrically connected to a case or shield of the connector assembly 700. Upon establishing 512, 516 the first and second electrical connections, an electrical circuit is established between the first probe 336 (e.g., first probe 620) and second probe 344 (e.g., second probe 632), where the electrical circuit passes through the first contact 140 (e.g., first contact of contact array 708 of FIG. 6a corresponding to graphical representation of first contact 616 in FIG. 6b), the cable assembly 112, the piezoelectric element 128 of array 124 in direct electrical communication with the first contact 140, and then back through the cable assembly 112 to the case or shield of connector 116 (e.g., connector 700 of FIG. 6a).

To determine 416 the value of the at least one electrical quantity of the electrical circuit established via the first and second electrical connection establishing steps 512, 516, the testing unit 304 (e.g., testing unit 604) may initially generate and send one or more electromagnetic signals (e.g., an electric current) at one or more appropriate frequencies corresponding to the particular acoustic device being tested (e.g., as just one example, 2-20 MHz) through the above-discussed electric circuit. For instance, generator 360 (e.g., computer-readable instructions, logic, etc.) of the testing unit 304 may trigger a battery 356 to generate any appropriate DC signal and pass the same through any appropriate circuitry of the testing unit 304 (e.g., DC-AC inverter, electric oscillator, not shown) configured to convert the DC signal into a corresponding AC signal. A determinator 364 of the testing unit 304 may then facilitate the taking of one or more direct measurements of any appropriate electrical quantities of the electrical circuit.

In one arrangement, a complex impedance through the electric circuit may be determined 416 across a range of operating frequencies and used to provide a range of information on failure types within the acoustic device (e.g., within the acoustic probe of FIG. 1). For instance, the determinator 364 may obtain in any appropriate manner the AC voltage of the electric circuit between the first and second probes 336, 344 and the AC current through the electric circuit and then determine the complex ratio of the obtained AC voltage to the obtained AC current to determine the complex impedance. As one example, the "real" or resistive part may be extracted or otherwise determined from the determined complex impedance, such as at the center of the corresponding frequency band specific to the particular acoustic device (e.g., at 11 MHz in the case of a 2-20 MHz range), and used to ascertain the viability of the particular piezoelectric element 128 that is directly electrically connected to the first contact 140 of the connector assembly 116 (e.g., first contact of connector assembly 700 of FIG. 6a). As another example, the capacitance (e.g., parallel capacitance) may be extracted or determined from the determined complex impedance and used to ascertain the viability of the of the cable assembly 112 that electrically interconnects the ultrasonic transducer 108 to the connector assembly 116.

With reference back to FIG. 4, the method 400 may then include ascertaining 420 a status of the acoustic device (e.g., of the ultrasonic probe of FIG. 1, i.e., of the ultrasonic transducer 108, the cable assembly 112, and/or the connector assembly 116) based at least in part on the one or more determined electrical quantities. In one arrangement, an analyzer 368 (e.g., computer-readable instructions, logic, etc.) of the testing unit 304 may obtain and utilize the acoustic device identifying information (e.g., type, manufacturer, etc.) to access and obtain corresponding electrical quality baseline (e.g., reference) values 372 (e.g., ranges, thresholds, etc.) from storage 320 and analyze the determined electrical quantities in view of the baseline electrical quantities to determine a status of the particular piezoelectric element 128 that is directly electrically connected to the first contact 140 and/or of the cable assembly 112.

For instance, the baseline resistive part of the complex impedance in the electrical circuit for a "good" or properly operating piezoelectric element 128 (e.g., in the middle of array 124) may, in one arrangement, be between about 25 to 60 Ohms. In this regard, the analyzer 368 may determine that the status of the particular piezoelectric element directly connected to the first contact is properly functioning (e.g., working above some threshold level of acceptability, etc.) when the determined resistance is within the baseline resistance range and not properly functioning (e.g., failed, not working above some threshold level of acceptability, etc.) when the determined resistance is not within the baseline resistance range. For instance, the resistive part of the determined complex impedance value is largely the result of dielectric losses in the material of the piezoelectric element 128 (e.g., rather than acoustic energy transmitted from the piezoelectric element 128). In this regard, a determined resistance value above the baseline resistance range may indicate that the corresponding piezoelectric element 128 has been damaged.

Of course, baseline resistance ranges may differ depending on where in the array 124 the particular piezoelectric element 128 is located, the particular type of piezoelectric element, the particular type of ultrasonic transducer 108, and/or the like. Baseline electrical quantities 372 may also be stored for other electrical quantities such as for the determined capacitance, where the analyzer 368 may determine that cable assembly 112 is properly functioning when the determined capacitance is within a corresponding baseline capacitance range and not properly functioning when the determined capacitance is not within the corresponding baseline capacitance range. The analyzer 368 may store results 376 of any analyses in storage 320 such as determined electrical quantities 380, statuses 384 of the acoustic device such as statuses 388 of one or more piezoelectric elements, a status 392 of the cable connector, and/or the like.

Figure 8:
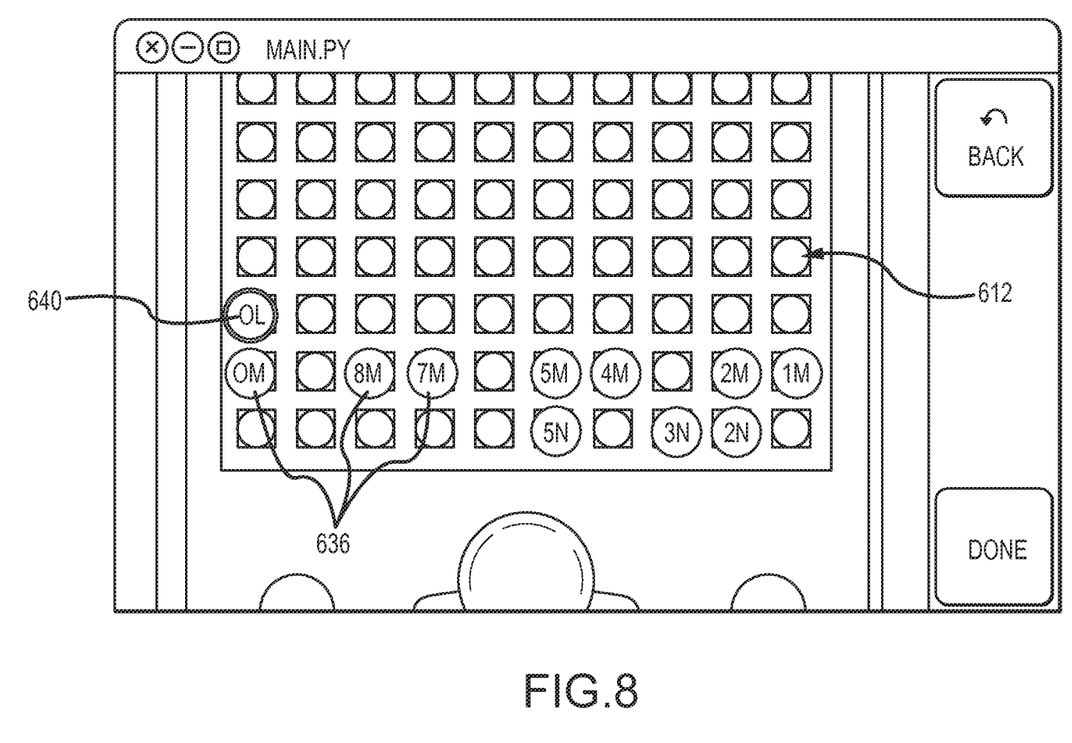
FIG. 8 is another screenshot of the display of FIG. 6.

Any determined statuses of the acoustic device (e.g., of the acoustic probe made up by the ultrasonic transducer 108, cable assembly 112, and connector assembly 116) may then be presented 424 on the display 308 of the testing unit 304 for receipt 520 by the user in any appropriate manner. As an example, FIG. 8 presents a screenshot of the graphical representation of the contact array 612 of FIGS. 6a-6b, where first and second types of graphical indications 636, 640 have been displayed over certain ones of the contacts of the contact array 612 to convey status information for the corresponding piezoelectric elements 128 of the contacts. For instance, the first graphical indication 636 may be in the form of a green circle to indicate that its corresponding piezoelectric element 128 is properly functioning while the second graphical indication 640 may be in the form of a yellow circle to indicate that its corresponding piezoelectric element 128 may not be properly functioning and thus needs to be further inspected or replaced. Of course, various other types graphical indications may be used to convey status information for the piezoelectric elements 128 (e.g., different colors, different patterns or shading, etc.). Furthermore, various additional granularities of status information of the piezoelectric elements 128, cable assembly 112, and the like based on one or more of the determined electrical quantities may be graphically displayed (e.g., failed, acceptable but not optimal level of performance, etc.).

Figure 6B:
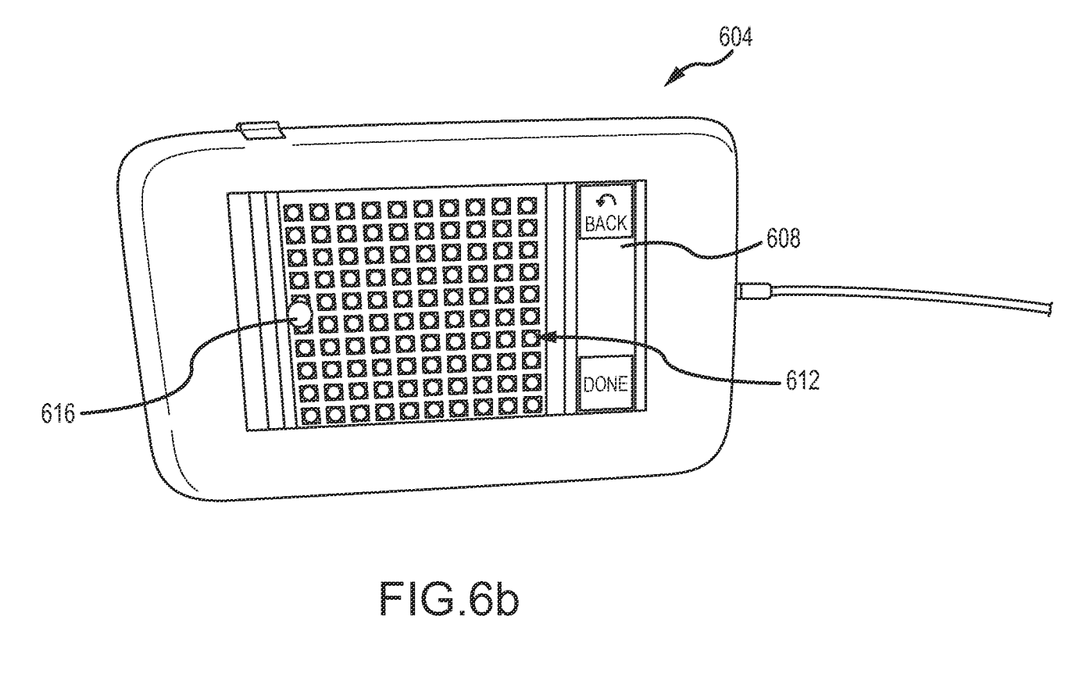

The user may manipulate the display 308 (e.g., the display 608 of FIGS. 6a-6b) in any appropriate manner to return to the screenshot illustrated in FIG. 6b at which point the testing unit 304 (e.g., testing unit 604) may modify 412 the graphical appearance of a second (or additional) contact of the contact array 612 (i.e., different than the first contact 616) in a manner different than that of the rest of the contacts in the contact array 612 which may be received 508 by a user. After the user has established 512 the first electrical connection with the second contact and has established 516 (if not already done so) the second electrical connection with the ground return path of the acoustic device (e.g., with the casing/shield of the connector assembly 116 (e.g., connector assembly 700 of FIG. 6a), the testing unit 304 (e.g., testing unit 604) may determine 416 the one or more electrical quantities of the newly created electrical circuit (e.g., which passes through the second contact rather than the first contact), ascertain 420 one or more statuses, and present 424 the status information for receipt 520 by the user as discussed previously. Of course, the user may appropriately test additional piezoelectric elements 128 of the array 124 in a similar manner.

In one arrangement, the user may be able to receive status information on the display 308 of the testing unit 304 immediately after each respective piezoelectric element 128 has been tested. Additionally or alternatively, the user may be able to receive collective status information for all of a particular number of piezoelectric elements 128 (e.g., corresponding to a particular region or area of the array 124 suspected to be improperly functioning or not functioning) after all of such piezoelectric elements 128 have been tested. For instance, the screenshot of FIG. 8 presents status information for a plurality of contacts of the contact array 612 (and thus for a respective plurality of the piezoelectric elements 128 of the array 124).

Figure 9:
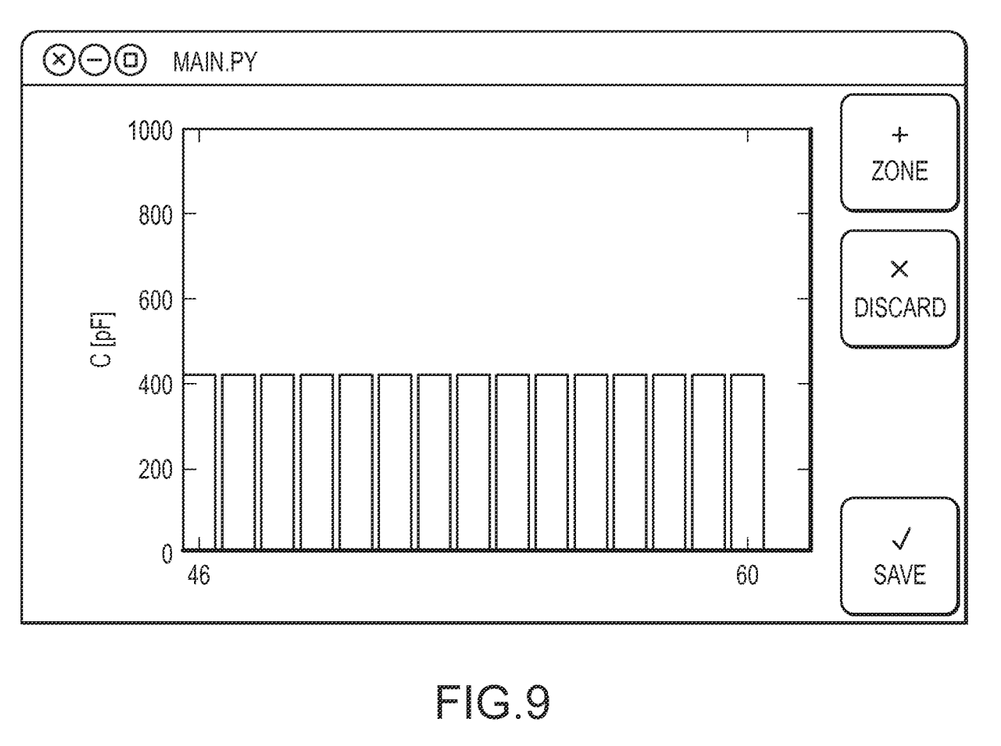
FIG. 9 is another screenshot of the display of FIG. 6.
Figure 10:
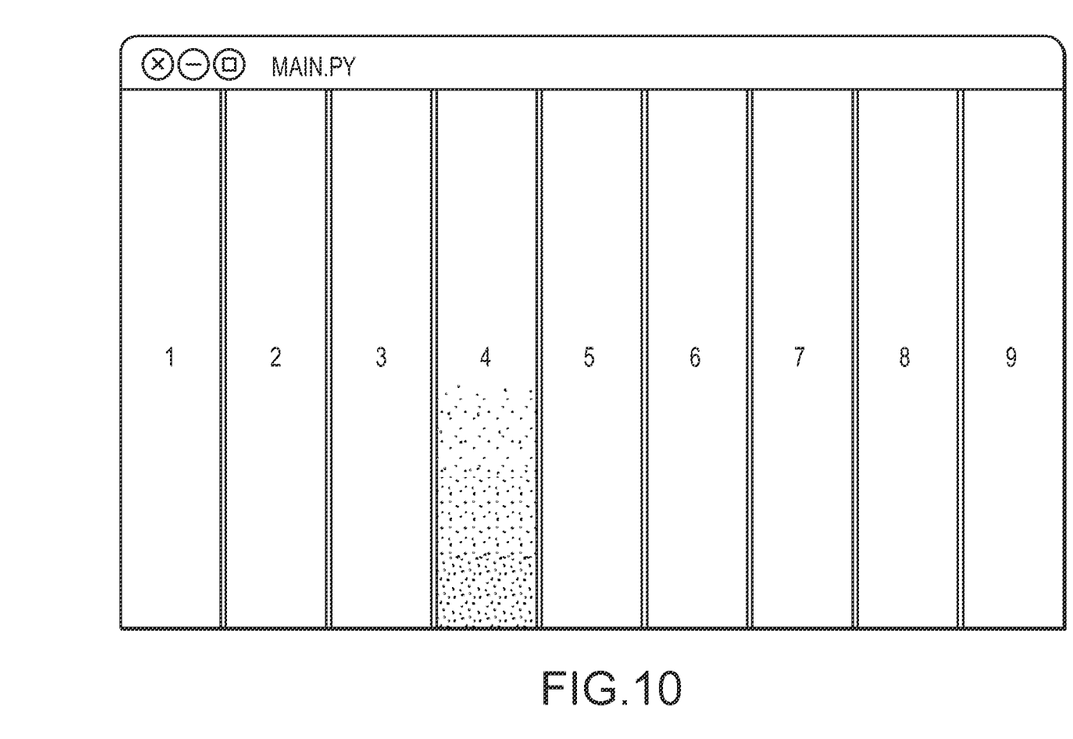
FIG. 10 is another screenshot of the display of FIG. 6.

The user may also be able to receive a graphical representation of one or more of the determined electrical quantities 380. For instance, FIG. 9 presents a screenshot of the display 608 that presents a plurality of determined capacitance values (in picofarads (pF)) of a respective plurality of electrical circuits that pass through a respective plurality of piezoelectric elements 128 numbered "46" through "60". FIG. 10 is a screenshot that illustrates a schematic representation of the aperture of the ultrasonic transducer 108 under test divided into groups or regions of piezoelectric elements 128 within the array 124. This screenshot allows an operator to select a specific region of the array where the operator believes a problem may exist for testing. For instance, selecting region "4" in FIG. 10 may cause the graphical representations of the corresponding piezoelectric elements 128 to be displayed for the operator. See FIGS. 6b and 8.

As discussed previously, the testing appliance 300 may advantageously be used to test a plurality of different acoustic devices such as acoustic probes having various different configurations of contact arrays 136. For instance, a user may input 504 any appropriate information into the testing unit 304 (e.g., electronic measurement instrument) that identifies a different acoustic probe which may be received 404 by the testing unit 304. Again, the display configurator 332 may use the received 404 acoustic probe identifying information to access a listing of contact array configurations 328 from storage 320 and then present 408 the same on display 308. The user may then utilize the testing appliance 300 to test the functionality of one or more components of the acoustic probe (e.g., one or more piezoelectric elements 128, the cable assembly 112, etc.) as discussed previously.

It will be readily appreciated that many additions and/or deviations may be made from the specific embodiments disclosed in the specification without departing from the spirit and scope of the invention. Furthermore, the illustrations and discussion herein has only been provided to assist the reader in understanding the various aspects of the present disclosure and that one or more various combinations of the above discussed arrangements and embodiments are also envisioned. Additionally, the various uses of "first," "second," etc. herein have only been provided to assist the reader in understanding the various functionalities presented herein and do not necessarily limit the scope thereof.

Embodiments disclosed herein can be implemented as one or more computer program products, i.e., one or more modules of computer program or computer-readable instructions encoded on a computer-readable medium for execution by, or to control the operation of, data processing apparatus. For example, the logic or software of the display configurator 332, generator 360, determinator 364 and analyzer 368 of the testing unit 304 may be loaded or read into memory 312 from storage 320 and executed by the processing unit 316. The storage 320 can be a machine-readable storage device, a machine-readable storage substrate, a non-volatile memory device, a composition of matter affecting a machine-readable propagated signal, or a combination of one or more of them. The computer program products may be written in any appropriate form of programming language including compiled or interpreted languages and it can be deployed in any form including as a stand-alone program or as a module, component, subroutine, or other unit suitable for use in a computing environment. A computer program can be deployed to be executed on one computer or on multiple computers that are located at one site or distributed across multiple sites and interconnected by a communication network.

The processes and logic flows can also be performed by, and apparatus can also be implemented as, special purpose logic circuitry, e.g., an FPGA (field programmable gate array) or an ASIC (application-specific integrated circuit). Processors suitable for the execution of a computer program may include, by way of example, both general and special purpose microprocessors, and any one or more processors of any kind of digital computer. Generally, a processor will receive instructions and data from a read-only memory or a random access memory or both. Generally, the elements of a computer are one or more processors for performing instructions and one or more memory devices for storing instructions and data. The techniques described herein may be implemented by a computer system configured to provide the functionality described.

While this specification contains many specifics, these should not be construed as limitations on the scope of the disclosure or of what may be claimed, but rather as descriptions of features specific to particular embodiments of the disclosure. Furthermore, certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The above described embodiments including the preferred embodiment and the best mode of the invention known to the inventor at the time of filing are given by illustrative examples only.

What is claimed is:

1. An appliance for testing the operation of an acoustic device that generates acoustic waves, the appliance comprising: a housing; circuitry disposed within the housing that is configured to determine one or more electrical quantities of an electrical circuit passing through a piezoelectric element of an acoustic device; a first probe electrically connected to the circuitry, wherein the first probe is electrically connectable to a contact of a contact array of the acoustic device that is electrically connected to the piezoelectric element via the electrical circuit; a second probe electrically connected to the circuitry, wherein the second probe is electrically connectable to a ground return path of the acoustic device via the electric circuit; and a display attached to the housing and in electrical communication with the circuitry, wherein the display is configured to present graphical images of the contact array and one or more values derived from the determined electrical quantities.

2. The appliance of claim 1, wherein the one or more electrical quantities include an AC voltage and an AC current between the first and second probes.

3. The appliance of claim 2, wherein the one or more values derived from the determined electrical quantities include at least one of capacitance or resistance between the first and second probes.

4. The appliance of claim 3, wherein the circuitry uses the determined electrical quantities to determine a complex impedance between the first and second probes, and wherein the circuitry uses the determined complex impedance to determine the at least one of the capacitance or the resistance between the first and second probes.

5. The appliance of claim 1, wherein the display presents graphical images of a first contact array of a first acoustic device and a second contact array of a second acoustic device different than the first acoustic device.

6. The appliance of claim 1, wherein the display presents a graphical indication of a status of one or more piezoelectric elements of the acoustic device based on the determined electrical quantities.

7. The appliance of claim 6, wherein the status is one of functioning at or above a threshold level of acceptability or not functioning above the threshold level of acceptability.

8. A method for use with the appliance of claim 1, the method comprising: presenting, on the display, a graphical representation of a contact array of a multi-contact connector of the acoustic device; modifying an appearance of a first contact of the contact array relative to another contact of the contact array on the display; determining, by the appliance, a value of at least one electrical quantity of an electrical circuit that passes through a first piezoelectric element of the acoustic device that is in direct electrical communication with the first contact; ascertaining, by the appliance based on the value of the at least one determined electrical quantity, a status of the acoustic device; and presenting, on the display, the status of the acoustic device.

9. The method of claim 8, wherein the at least one electrical quantity is an AC voltage and an AC current through the electrical circuit, and wherein the ascertaining step includes: deriving, by the appliance, at least one additional electrical quantity from the AC voltage and the AC current through the electrical circuit; and ascertaining, by the appliance based on the at least one additional quantity the status of the acoustic device.

10. The method of claim 9, wherein the at least one additional electrical quantity includes at least one of capacitance or resistance through the electrical circuit.

11. The method of claim 10, wherein the deriving includes:
determining, by the appliance using the AC voltage and the AC current through the electrical circuit, a complex impedance through the electrical circuit; and
determining, by the appliance using the complex impedance through the electrical circuit, the at least one of the capacitance or resistance through the electrical circuit.

12. The method of claim 9, wherein the ascertaining step includes:
querying whether the value of the at least one additional electrical quantity is within a reference range of the additional electrical quantity;
establishing that the status is a first status in response to the of the at least one additional electrical quantity being within the reference range of the additional electrical quantity
establishing that the status is a second status in response to the of the at least one additional electrical quantity not being within the reference range of the additional electrical quantity.

13. The method of claim 8, wherein the status is the status of the first piezoelectric element.

14. The method of claim 8, wherein the first piezoelectric element is disposed on a transducer head of the acoustic device, and wherein the status is the status of a cable assembly that electrically connects the transducer head to the multi-contact connector.

15. The method of claim 8, wherein the presenting step includes:
presenting a graphical representation of at least the first piezoelectric element; and modifying an appearance of the graphical representation of at least the first piezoelectric element to indicate the status of the first piezoelectric element.

16. The method of claim 15, wherein the presenting step includes presenting a graphical representation of a plurality of piezoelectric elements of the acoustic device, wherein the first piezoelectric element is one of the plurality of piezoelectric elements.

17. The method of claim 8, further including: modifying an appearance of a second contact of the contact array relative to other contacts of the contact array on the display; determining, by the appliance, a value of at least one electrical quantity of an electrical circuit that passes through a second piezoelectric element of the acoustic device that is in direct electrical communication with the second contact; ascertaining, by the appliance based on the value of the at least one determined electrical quantity, a status of the acoustic device; and presenting, on the display, the status of the acoustic device.

18. The method of claim 8, wherein the acoustic device is a first acoustic device, and wherein the method further includes: presenting, on the display, a graphical representation of a contact array of a multi-contact connector of a second acoustic device, wherein the graphical representations of the contact array of the second acoustic device is different that the graphical representations of the contact array of the first acoustic device; modifying an appearance of a first contact of the contact array of the second acoustic device relative to other contacts of the contact array of the second acoustic device on the display; determining, by the appliance, a value of at least one electrical quantity of an electrical circuit that passes through a first piezoelectric element of the second acoustic device that is in direct electrical communication with the first contact of the second acoustic device; ascertaining, by the appliance based on the value of the at least one determined electrical quantity, a status of the second acoustic device; and presenting, on the display, the status of the second acoustic device.

19. The method of claim 8, further including before the determining step:
sending an electric current through the electronic circuit.

20. A method for use with the appliance of claim 1, the method comprising: first receiving, from the display, a graphical indication of the contact array of the acoustic device to be tested, wherein the graphical indication of the contact array includes a graphical indication of a first contact of the contact array, and wherein the graphical indication of the first contact is different than the graphical indication of other contacts of the pin array; establishing a first electrical connection between the first probe of the appliance and the first contact of the acoustic device; establishing a second electrical connection between the second probe of the appliance and the ground return path of the acoustic device; and second receiving, from the display, in response to the established first and second electrical connections, a graphical indication of a status of the acoustic device.

21. The method of claim 20, wherein the second receiving step includes:
receiving a graphical indication of a status of a first piezoelectric element of a piezoelectric element array of the acoustic device, wherein the first piezoelectric element is in direct electrical communication with the first contact.

22. The method of claim 21, further including after the second receiving step: third receiving, from the display, a graphical indication of a second contact of the contact array of the acoustic device; establishing a third electrical connection between the first probe of the appliance and the third contact of the acoustic device; establishing a fourth electrical connection between the second probe of the appliance and a ground lead of the acoustic device; and fourth receiving, from the display, in response to the established third and fourth electrical connections, a graphical indication of a status of a second piezoelectric element of the piezoelectric element array of the acoustic device, wherein the second piezoelectric element is in direct electrical communication with the second contact.

23. The method of claim 20, wherein the second receiving step includes:
receiving a graphical indication of a status of an electrical connection between a first piezoelectric element of a piezoelectric element array of the acoustic device and the first contact.

24. The method claim 20, further including before the first receiving step:
inputting, into the appliance, information identifying the acoustic device to be tested, wherein the graphical indication of the contact array corresponds to the inputted identifying information.

25. The method of claim 24, wherein the acoustic device is a first acoustic device, and wherein the method further includes after the second receiving step:
inputting, into the appliance, information identifying a second acoustic device to be tested, wherein the second acoustic device is different than the first acoustic device;
first receiving, from the display, a graphical indication of a contact array of the second acoustic device corresponding to the inputted identifying information, wherein the graphical indication of the contact array includes a graphical indication of a first contact of the contact array, and wherein the graphical indication of the first contact is different than the graphical indication of other contacts of the contact array;
establishing a first electrical connection between the first probe of the appliance and the first contact of the second acoustic device;
establishing a second electrical connection between the second probe of the appliance and a ground lead of the second acoustic device; and
second receiving, from the display, in response to the established first and second electrical connections, a graphical indication of a status of the second acoustic device.

* * * * *

UNITED STATES PATENT AND TRADEMARK OFFICE
CERTIFICATE OF CORRECTION

| | | |
|---|---|---|
| PATENT NO. | : 9,513,327 B2 | Page 1 of 1 |
| APPLICATION NO. | : 14/336117 | |
| DATED | : December 6, 2016 | |
| INVENTOR(S) | : Gessert et al. | |

It is certified that error appears in the above-identified patent and that said Letters Patent is hereby corrected as shown below:

In the Claims

Column 12, Line 31, delete "quantity" and insert therefore --electrical quantity,--

Column 14, Line 13, delete "a ground lead" and insert therefore --the ground return path--

Signed and Sealed this
Twenty-eighth Day of February, 2017

Michelle K. Lee
*Director of the United States Patent and Trademark Office*